(12) United States Patent
Sharratt et al.

(10) Patent No.: US 7,153,397 B2
(45) Date of Patent: Dec. 26, 2006

(54) PROCESS FOR THE PURIFICATION OF FLUOROMETHYL HEXAFLUOROISOPROPYL ETHER

(75) Inventors: Andrew Paul Sharratt, Cheshire (GB); Lee Colin Draper, Flintshire (GB)

(73) Assignee: Ineos Fluor Holdings Limited, Runcorn (GB)

(*) Notice: Subject to any disclaimer, the term of this patent is extended or adjusted under 35 U.S.C. 154(b) by 319 days.

(21) Appl. No.: 10/451,264

(22) PCT Filed: Dec. 21, 2001

(86) PCT No.: PCT/GB01/05729

§ 371 (c)(1),
(2), (4) Date: Dec. 8, 2003

(87) PCT Pub. No.: WO02/50005

PCT Pub. Date: Jun. 27, 2002

(65) Prior Publication Data

US 2004/0124076 A1     Jul. 1, 2004

(30) Foreign Application Priority Data

Dec. 21, 2000 (GB) .................................. 0031310.6

(51) Int. Cl.
*B01D 3/34* (2006.01)
*C07C 41/00* (2006.01)

(52) U.S. Cl. ................. 203/57; 203/59; 203/64; 203/67; 203/DIG. 25; 568/682; 568/683

(58) Field of Classification Search ............. 203/59, 203/57, 63, DIG. 25, 64, 67; 568/674, 682, 568/579, 913, 683
See application file for complete search history.

(56) References Cited

U.S. PATENT DOCUMENTS

| 4,250,334 A | * | 2/1981 | Coon et al. ............. 568/683 |
| 4,328,376 A | | 5/1982 | Berger et al. ........... 568/682 |
| 4,469,898 A | * | 9/1984 | Coon et al. ............. 568/683 |
| 5,684,210 A | * | 11/1997 | Kawai et al. ........... 568/682 |

FOREIGN PATENT DOCUMENTS

WO     WO 99/44978      9/1999

* cited by examiner

*Primary Examiner*—Virginia Manoharan
(74) *Attorney, Agent, or Firm*—Morgan Lewis & Bockius LLP

(57) ABSTRACT

A process for the purification of fluoromethyl hexafluoroisopropyl ether which comprises contacting a crude composition comprising fluoromethyl hexafluoroisopropyl ether and hexafluoroisopropyl alcohol with a modifier in the presence of which the vapor pressure of the ether and/or the alcohol is modified whereby the difference in vapor pressure of the ether and the alcohol increases relative to the difference in vapor pressure of the ether and alcohol in the absence of the modifier and separating the ether from the alcohol.

15 Claims, 1 Drawing Sheet

PROCESS FOR THE PURIFICATION OF FLUOROMETHYL HEXAFLUOROISOPROPYL ETHER

Figure 1:
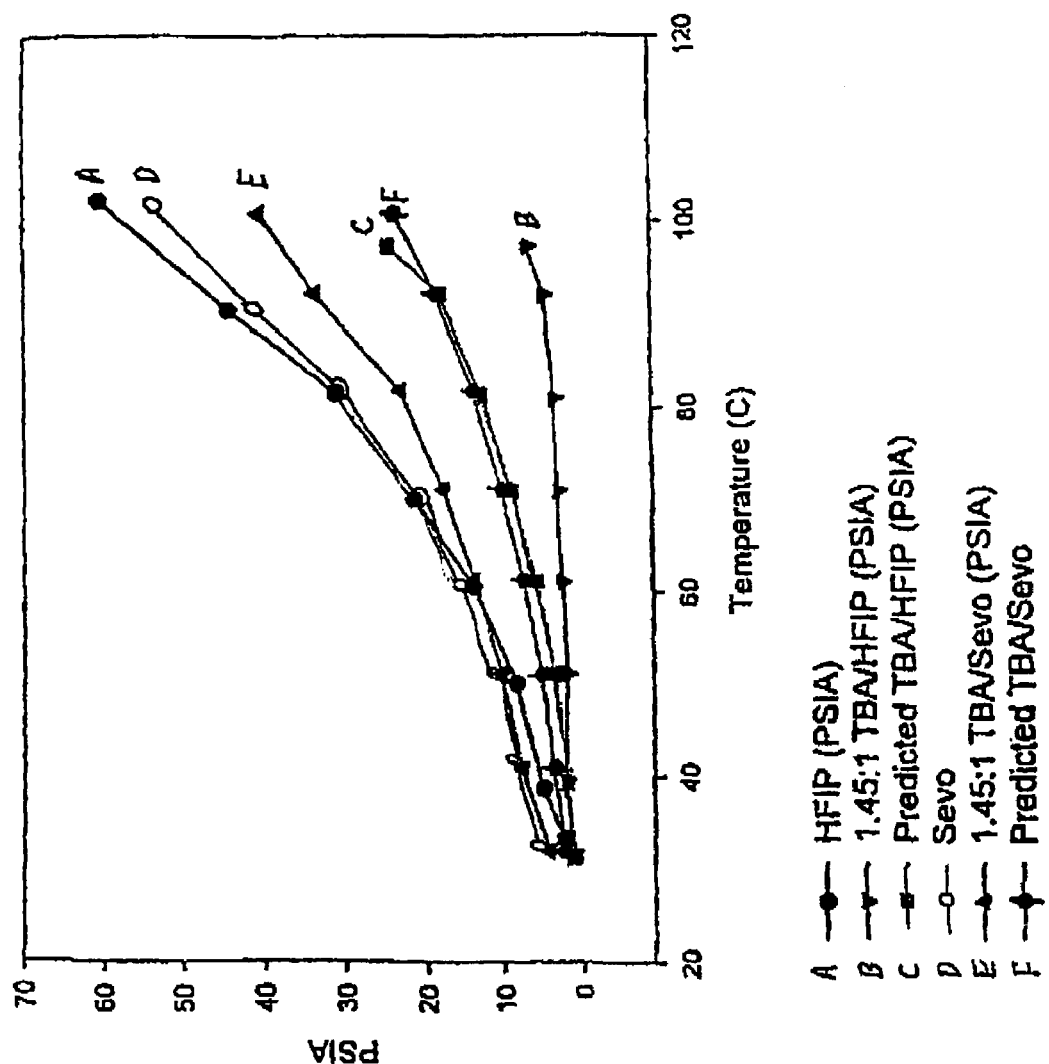

This invention relates to a process for the purification of fluoromethylhexafluoroisopropylether of formula $CH_2FOCH(CF_3)_2$ which has anaesthetic properties and is known as "Sevoflurane".

It is known that Sevoflurane may be produced by the reaction of formaldehyde, hydrogen fluoride and hexafluoroisopropyl alcohol $(CF_3)_2CHOH$ (HFIP). It is also known to produce Sevoflurane from bis (fluoromethyl) ether and hexafluoroisopropyl alcohol. U.S. Pat. No. 4,250,334 describes a process in which hexafluoroisopropyl alcohol is added to a mixture of a stoichiometric excess of paraformaldehyde and hydrogen fluoride plus sufficient sulphuric acid to sequester most of the water formed. WO97/25303 describes a process for the production of Sevoflurane in which essentially pure bis(fluoromethyl) ether is reacted with hexafluoroisopropyl alcohol. Due to the chemical structure of Sevoflurane, HFIP is typically employed as a reactant to provide the hexafluoropropyl moiety in Sevoflurane.

However, in producing Sevoflurane, unreacted HFIP may be present in the reaction mixture. It is necessary to remove HFIP from Sevoflurane which, for medical use, has typically to be produced to a high level of purity. The boiling points of HFIP and Sevoflurane are similar and conventional separation by distillation does not present an attractive option as HFIP and Sevoflurane would distil together possibly as an azeotrope. Other methods of separation of these materials have been developed, for example aqueous washing. Such methods are typically not especially efficient and are costly.

WO 99/44978 describes a process to remove HFIP from crude Sevoflurane and involves employing an aqueous alkaline wash and several process stages thus introducing complexity into the purification process which increases costs and requires a high level of process control.

It has now been found that difficulties encountered in removing unreacted HFIP from Sevoflurane may be reduced or avoided by using a modifier which interacts selectively with HFIP and permits purification of Sevoflurane by distillation.

According to the present invention there is provided a process for the purification of fluoromethyl hexafluoroisopropyl ether which comprises contacting a crude composition comprising fluoromethyl hexafluoroisopropyl ether and hexafluoroisopropyl alcohol with a modifier in the presence of which the vapour pressure of the said ether and/or the said alcohol is modified whereby the difference in vapour pressure of the ether and the alcohol increases relative to the difference in vapour pressure of the ether and alcohol in the absence of the modifier and separating the ether from the alcohol, preferably by heating the mixture comprising the modifier and the said crude composition to effect distillation of the ether or the alcohol.

Preferably, the modifier acts to reduce the vapour pressure of HFIP to a greater degree than it reduces that of Sevoflurane so as to enable Sevoflurane to be distilled from the crude composition. Although a modifier which preferentially reduces the vapour pressure of Sevoflurane could be employed, so permitting removal of HFIP by distillation, Sevoflurane would still have to be removed from the crude composition.

Suitably the modifier comprises a functional group which preferentially interacts with HFIP rather than Sevoflurane and preferably comprises a nucleophillic substance, for example a substance which is capable of donating electrons to HFIP or a substance capable of bonding, for example hydrogen-bonding, preferentially with HFIP. Preferably, the modifier comprises ammonia and/or an amine. Suitable amines include primary amines, secondary and tertiary amines. Quaternary amines may also be employed. The amine may be aliphatic, for example diethyl amine, hexyl amine and dodecylamine and especially tributyl amine and tripentyl amine; aromatic, for example aniline and pyridine; or alicyclic, for example piperidine. The amine may be saturated or unsaturated, for example melamine. In an especially preferred embodiment, the modifier is selected from aliphatic amines, for example tributyl amine and aromatic amines, for example aniline Other suitable modifiers include amine derivatives of the amines set out hereabove, amides, amidines and alcohols including primary, secondary and/or tertiary compounds from these groups. The modifier may contain two or more different functional groups for example, amine, amidine, amide, carbonyl, hydroxyl, thiol and halogen groups and beneficially may assist in the removal of additional components to HFIP from the crude composition, for example BFME. If desired the modifier may be provided on a support, for example a functionalised resin, for ease and efficiency of contact with the crude Sevoflurane composition.

In an especially preferred embodiment the modifier comprises an unsubstituted tertiary alkyl amine.

The modifier may comprise a substituted amine, preferably a hydroxyalkyl amine and/or a halogenated alkyl amine for example a fluorinated amine. The modifier may also comprise an amine hydrofluorde especially an amine hydrofluoride having from 2 to 10 moles of hydrogen fluoride per mole of amine. Where the modifier contains an alkyl group, the alkyl group preferably contains from 3 to 12 carbon atoms, for example butyl.

Suitably the modifier has a high boiling point relative to Sevoflurane so as to reduce the level or avoid entirely the presence of the modifier in the purified Sevoflurane. Modifiers, especially amines having a relatively high boiling point are especially preferred and desirably the modifier has a boiling point of at least 100° C. and especially at least 150° C. so as to reduce the drawback of undesirable odours being present in the Sevoflurane.

Additional components to HFIP in the crude composition may be separated from the composition by contact with the modifier, for example hydrogen fluoride and BFME. If present, additional components to HFIP may be separated from Sevoflurane in the crude composition by physical methods, for example distillation, due to differences in vapour pressure between the additional component and Sevoflurane, or by chemical reaction so that the additional component is modified and separation from Sevoflurane rendered easier. For example an alcohol group may suitably be included in the modifier in order to promote reaction with BFME so permitting removal from Sevoflurane of BFME or material derived from the reaction of BFME.

The modifier may be contacted with the crude composition at a molar ratio of modifier to Sevoflurane or HFIP of at least 0.1:1, preferably at least 0.5:1 and especially at least 1:1. Desirably the molar ratio of the modifier to Sevoflurane or HFIP is suitably not more than 3:1. The ratio is to be calculated on the total amount of Sevoflurane and HFIP where both are present.

The crude Sevoflurane composition and the modifier may be contacted in the liquid or gas phase. Where Sevoflurane is in the liquid phase, the pressure in the contacting step may be regulated so as to control the boiling of Sevoflurane. The modifier and crude Sevoflurane composition may be contacted in conventional equipment including a stirred mixing tank, in-line static flow mixing apparatus, jet mixing apparatus and venturi eductors. Depending on the process design, the apparatus for contacting the crude Sevoflurane composition and the modifier may include heat exchange apparatus to effect heat transfer to or from the mixture.

The crude Sevoflurane composition may be in the vapour phase and contacted with the modifier. Apparatus suitable for gas-liquid phase contact may be employed, by way of example, a bubble column, distillation column, absorption column and falling film absorption apparatus. The apparatus may suitably be adapted to provide for heat exchange to an external heat transfer medium.

In separating Sevoflurane from HFIP, the modifier suitably remains with HFIP and Sevoflurane is evaporated from the mixture of the crude composition and modifier. Preferably the combination of HFIP and modifier is subjected to regeneration to obtain desirably pure HFIP, Suitably the purified HFIP is recycled to the upstream part of the process for re-use as a feed stock in the production of the crude composition.

An acid may be employed to subsequently remove the modifier from the Sevoflurane or HFIP. Suitable acids include Bronsted acids, for xample sulphuric acid, hydrogen fluoride, phosphoric acid, hydrochloric acid, trifluoromethane sulphonic acid and fluorosulphonic acid, suitably in liquid form or as a supported resin, acidic adsorbents, and organic acids for example acetic acid and citric acid. The modifier may also be removed by conventional techniques including distillation, evaporation and condensation. Preferably the modifier has a vapour pressure which is low relative to that of HFIP. HFIP may be removed from the modifier through distillation, optionally under reduced pressure so as to obtain the modifier in the purified form. The modifier may then be recycled to the process for contact with the crude Sevoflurane composition. If desired, the modifier and HFIP may be separated in a plurality of stages so as to reduce temperature differences over any part of the separation apparatus. Conventional separation apparatus for example bayonet tube vaporisers, falling film heat exchangers and kettle boilers, may be employed as desired.

The crude Sevoflurane composition may be produced by any known route involving the use of HFIP. Preferably, purified Sevoflurane is produced by a process which comprises reacting BFME and HFIP together, optimally in the presence of an acid, preferably a Lewis or Bronsted acid, for example sulphuric acid, to produce a crude composition comprising fluoromethyl hexafluoroisopropyl ether and unreacted HFIP, mixing the crude composition with a modifier and distilling the mixture so as to recover fluoromethyl hexafluoroisopropyl ether from the crude composition.

The reaction between the bis(fluoromethyl) ether and the hexafluoroisopropyl alcohol is conveniently carried out at a temperature of less than 50° C., preferably 10 to 40° C. especially 15 to 35° C., Suitably the reaction is carried out at atmospheric pressure, although if desired subatmospheric or superatmospheric pressure.

BFME may be employed as is without purification and advantageously enables the operation of an integrated process including the production of BFME and its direct use as a feedstock to produce Sevoflurane. Alternatively, BFME may be treated so as to purify it partly or wholly prior to use in the process according to the invention. If desired, bis (fluoromethyl) ether may be separated from the reaction mixture and treated to produce essentially pure bis(fluoromethyl) ether which may then be reacted with hexafluoroisopropyl alcohol to produce fluoromethylhexafluoroisopropylether. Formaldehyde and/or hydrogen fluoride may be fed to the process of the invention in addition to BFME and HFIP as desired.

If desired, Sevoflurane may also be produced by contacting formaldehyde or a polymeric form thereof such as paraformaldehyde or trioxane with HF and HFIP, for example as described in U.S. Pat. No. 4,250,334. The crude composition may comprise other components in addition to Sevoflurane and HFIP including hydrogen fluoride, acetals, formates, formaldehyde in any of its known forms and polyethers, for example $(CF_3)_2CHOCH_2OCH_2F$ and $((CF_3)_2CHO)_2CH_2$.

The process for producing the crude composition and separating Sevoflurane from it may be operated as a batch or continuous process or a combination thereof but is preferably operated as a batch process.

BFME may be produced by reaction of formaldehyde (or a polymeric form of formaldehyde such as paraformaldehyde or trioxane) with hydrogen fluoride. Any of the known methods for production of the bis(fluoromethyl) ether may be employed as the ether formation step. The production of bis(fluoromethyl) ether from formaldehyde and hydrogen fluoride is described, for example, in EP-A-518506 and in WO 93/10070, WO 93/12057 and WO 93/22265, for example. The disclosures of these publications are incorporated herein by reference, The ether production process described in WO 93/10070 is especially preferred and comprises reacting formaldehyde with hydrogen fluoride in a reaction-distillation column from which the ether is withdrawn in essentially pure form and in particular essentially free from water.

FIG. 1 shows a plot of measured and predicted vapour pressures against temperature for pure Sevoflurane ("Sevo"), pure HFIP and mixtures of tributylamine with Sevoflurane and tributylamine with HFIP.

The invention is illustrated but in no way limited by the following Examples

EXAMPLE 1

The single component vapour pressures of HFIP and Sevo were measured at a range of temperatures in a sealed system. These were compared with the measured vapour pressures over a mixture of 1.45:1 t-butyl amine with Sevoflurane and tributyl amine with HFIP. The results are plotted in FIG. 1. In addition, the predicted vapour pressures of these mixtures were plotted on FIG. 1. In the presence of the modifier the vapour pressure of HFIP was reduced relative to the predicted vapour pressure and almost completely suppressed. The vapour pressure of Sevoflurane was higher than the predicted vapour pressure.

EXAMPLE 2

2 ml (2.9 g) of a mixture of Sevoflurane (4 g) and TBA (5.48 g) was placed in a flask to which 0.8 g HFIP was added. The mixture was heated to about 88° C. and stirred and the distilled favours were collected and analysed. The composition of the analysed product contained 98.3% by weight of Sevoflurane and 1.7% HFIP. The procedure was repeated without the modifier and the product recovered contained 71.2% Sevoflurane and 38.8% HFIP illustrating that use of the modifier enabled Sevoflurane of a high purity to be recovered.

EXAMPLE 3

A mixture containing 1.54 g Sevoflurane and 0.5 g HFIP was heated to about 55° C. and the distilled vapours were collected and analysed. The composition of the product analysed was the same as that of the original mixture.

0.5 ml of TBA was added to the distilate, the mixture re-distilled and the vapours analysed. The level of HFIP in this distilled composition was reduced by 85% relative to the level of HFIP in the first distillate.

The invention claimed is:

1. A process for the purification of fluoromethyl hexafluoroisopropyl ether which comprises contacting a crude composition comprising fluoromethyl hexafluoroisopropyl ether and hexafluoroisopropyl alcohol (HFIP) with a modifier comprising a substance which donates electrons to HFIP or a substance which preferentially bonds with HFIP thereby modifying the vapor pressure of said ether and/or said alcohol whereby the difference in vapor pressure of the ether and the alcohol increases relative to the difference in vapor pressure of the ether and alcohol in the absence of the modifier and distilling to separate the ether from the alcohol, said modifier comprising at least one member of the group consisting of ammonia and an amine.

2. A process as claimed in claim 1 which comprises separating the ether from the alcohol by heating the mixture comprising the modifier and said crude composition to effect distillation of the ether or the alcohol.

3. A process as claimed in claim 1 in which the modifier is an aliphatic amine or aromatic amine.

4. A process as claimed in claim 3 in which the modifier is tributyl amine, tripentyl amine or aniline.

5. A process as claimed in claim 3 in which the modifier contains two or more different functional groups selected from the group consisting of amine, amidine, amide, carbonyl, hydroxyl, thiol and halogen groups.

6. A process as claimed in claim 1 which comprises contacting the modifier with the crude composition at a molar ratio of modifier to moles of fluoromethyl hexafluoroisopropyl ether and hexafluoroisopropyl alcohol together of at least 0.1:1.

7. A process as claimed in claim 1 which comprises heating the crude composition whereby fluoromethyl hexafluoroisopropyl ether is separated from the modifier and hexafluoroisopropyl alcohol.

8. A process as claimed in claim 7 which comprises subjecting the residue of hexafluoroisopropyl alcohol and modifier to regeneration to obtain purified hexafluoroisopropyl alcohol.

9. A process as claimed in claim 7 which comprises contacting the separated fluoromethyl hexafluoroisopropyl ether with acid to remove any modifier present in the fluoromethyl hexafluoroisopropyl ether.

10. A process as claimed in claim 1 which comprises producing the crude composition by contacting formaldehyde or a polymeric form thereof with hydrogen fluoride and hexafluoroisopropyl alcohol.

11. A process as claimed in claim 1 which comprises producing the crude composition by reacting bis fluoromethyl ether and hexafluoroisopropyl alcohol together in the presence of an acid.

12. A process for the purification of fluoromethyl hexafluoroisopropyl ether which comprises reacting bis fluoromethyl ether and hexafluoroisopropyl alcohol (HFIP) together in the presence of an acid to produce a crude composition comprising fluoromethyl hexafluoroisopropyl ether and unreacted hexafluoroisopropyl alcohol, mixing the crude composition with a modifier comprising a substance which is capable of donating electrons to HFIP or a substance capable of bonding preferentially with HFIP and distilling the mixture so as to recover fluoromethyl hexafluoroisopropyl ether from the crude composition, said modifier comprising at least one member of the group consisting of ammonia and an amine.

13. A process as claimed in claim 12 in which the vapor pressure of the the hexafluoroisopropyl alcohol is modified in the presence of the modifier whereby the difference in vapor pressure of the ether and the alcohol increases relative to the difference in vapor pressure of the ether and alcohol in the absence of the modifier and separating the ether from the alcohol.

14. A process as claimed in claim 11 or claim 12 which comprises reacting the bis(fluoromethyl) ether and the hexafluoroisopropyl alcohol together at a temperature of less than 50° C.

15. A process as claimed in claim 11 or claim 12 in which the bis(fluoromethyl) ether is essentially pure.

* * * * *